(12) United States Patent
Konno

(10) Patent No.: US 10,860,174 B2
(45) Date of Patent: Dec. 8, 2020

(54) BIOLOGICAL INFORMATION DISPLAYING APPARATUS

(71) Applicant: NIHON KOHDEN CORPORATION, Tokyo (JP)

(72) Inventor: Norihito Konno, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 782 days.

(21) Appl. No.: 14/944,914

(22) Filed: Nov. 18, 2015

(65) Prior Publication Data

US 2016/0147385 A1    May 26, 2016

(30) Foreign Application Priority Data

Nov. 25, 2014   (JP) ................... 2014-237287

(51) Int. Cl.
*G06F 3/0482* (2013.01)
*A61B 5/00* (2006.01)

(52) U.S. Cl.
CPC ............ *G06F 3/0482* (2013.01); *A61B 5/743* (2013.01); *A61B 5/7435* (2013.01)

(58) Field of Classification Search
CPC .......... G06F 3/0482; A61B 5/00; A61B 5/743
See application file for complete search history.

(56) References Cited

U.S. PATENT DOCUMENTS

| | | | |
|---|---|---|---|
| 4,862,498 A * | 8/1989 | Reed ..................... | G06F 3/0482 379/355.09 |
| 6,232,972 B1 * | 5/2001 | Arcuri .................... | G06F 9/453 715/815 |

(Continued)

FOREIGN PATENT DOCUMENTS

| | | |
|---|---|---|
| JP | 2001-005585 A | 1/2001 |
| JP | 2003-029893 A | 1/2003 |

(Continued)

OTHER PUBLICATIONS

Constantine Stephanidis, Alex Paramythis, Michael Sfyrakis, A. Stergiou, N. Maou, A. Leventis, G. Paparoulis, and Charalampos Karagiannidis. 1998. Adaptable and Adaptive User Interfaces for Disabled Users in the AVANTI Project.*
Findlater, L., McGrenere, J. A comparison of static, adaptive, and adaptable menus. In Proceedings of Computer-Interaction, 2004, 89-96 (Year: 2004).*
Japanese Office Action issued in Patent Application No. JP-2014-237287 dated Apr. 3, 2018.

*Primary Examiner* — Andrea N Long
(74) *Attorney, Agent, or Firm* — Pearne & Gordon LLP

(57) ABSTRACT

A biological information displaying apparatus which is configured to display biological information measured by a sensor adapted to be attached to a patient, includes: a displaying unit which is configured to display the biological information on a screen; an operation menu storing unit which is configured to store a plurality of operation menus for operating the biological information displaying apparatus; an operation menu priority determining unit which is configured to determine priorities of the operation menus stored in the operation menu storing unit, based on a predetermined condition; and a preferential-shortcut menu displaying unit which, based on the priorities determined by the operation menu priority determining unit, is configured to select a first part of the operation menus as a first shortcut menu, and which is configured to display the first shortcut menu on the screen.

11 Claims, 8 Drawing Sheets

(56) References Cited

U.S. PATENT DOCUMENTS

| | | | | |
|---|---|---|---|---|
| 6,305,373 B1* | 10/2001 | Wallace | ............ | A61M 16/0051 |
| | | | | 128/204.21 |
| 6,624,831 B1* | 9/2003 | Shahine | ................ | G06F 3/0482 |
| | | | | 715/811 |
| 8,020,104 B2* | 9/2011 | Robarts | ................ | G06F 21/606 |
| | | | | 715/744 |
| 9,213,466 B2* | 12/2015 | Homburg | ............... | G06F 3/0482 |
| 2002/0111932 A1* | 8/2002 | Roberge | ................ | G16H 40/63 |
| 2003/0007012 A1* | 1/2003 | Bate | ...................... | G06F 3/0482 |
| | | | | 715/825 |
| 2006/0004680 A1* | 1/2006 | Robarts | ................ | G06N 3/004 |
| | | | | 706/12 |
| 2006/0099947 A1* | 5/2006 | Shozaki | ............. | H04L 61/1523 |
| | | | | 455/435.1 |
| 2007/0192725 A1* | 8/2007 | Chen | ........................ | G06F 9/451 |
| | | | | 715/779 |
| 2008/0320419 A1* | 12/2008 | Matas | ............... | H04M 1/72572 |
| | | | | 715/863 |
| 2009/0007020 A1* | 1/2009 | Suzuki | ................. | G06F 3/0482 |
| | | | | 715/841 |
| 2009/0054743 A1* | 2/2009 | Stewart | ................... | G16H 15/00 |
| | | | | 600/301 |
| 2009/0158167 A1* | 6/2009 | Wang | .................... | G06F 3/0482 |
| | | | | 715/745 |
| 2011/0080293 A1 | 4/2011 | Tanishima et al. | | |
| 2011/0320984 A1* | 12/2011 | Irani | ..................... | G06F 3/0482 |
| | | | | 715/841 |
| 2012/0226117 A1* | 9/2012 | Lamego | ............... | A61B 5/7475 |
| | | | | 600/316 |
| 2013/0198685 A1* | 8/2013 | Bernini | .................. | G16H 40/63 |
| | | | | 715/800 |
| 2014/0096024 A1* | 4/2014 | Laurent | .................. | G06F 21/31 |
| | | | | 715/739 |
| 2015/0120317 A1* | 4/2015 | Mayou | ................... | G09B 19/00 |
| | | | | 705/2 |

FOREIGN PATENT DOCUMENTS

| | | |
|---|---|---|
| JP | 2010-061692 A | 3/2010 |
| JP | 2011-098189 A | 5/2011 |
| JP | 2014-176498 A | 9/2014 |

* cited by examiner

BIOLOGICAL INFORMATION DISPLAYING APPARATUS

CROSS-REFERENCE TO RELATED APPLICATION(S)

This application is based upon and claims the benefit of priority from prior Japanese patent application No. 2014-237287, filed on Nov. 25, 2014, the entire contents of which are incorporated herein by reference.

BACKGROUND

The presently disclosed subject matter relates to a biological information displaying apparatus such as a bedside monitor which is installed at a bed side or the like, and which can display various kinds of treatment assistance information including biological information of a patient in a list form.

In a medical facility such as a hospital, in order to monitor the condition of a patient under treatment, a biological information displaying apparatus which can comprehensively display biological information of the patient is widely used.

Such a biological information displaying apparatus is usually called a bedside monitor, and installed on a side of a bed for a patient in a medical ward, a CCU, an ICU, a surgery room, or the like. A bedside monitor displays measurement values and waveforms of biological information such as the heart rate, blood pressure, respiratory rate, and the like acquired from the patient, on one screen in an easily visible manner or in a list form. A medical person (for example, the doctor or the nurse) can know the condition of the patient at a glance to the display.

In a bedside monitor, furthermore, settings, i.e., the kinds (e.g., the blood pressure and the respiratory rate) of biological information to be displayed on a basic screen, the display method (e.g., the display position, and the display color), a monitor alarm (sound, the display method, and the like) can be variously customized in accordance with the place of use, the purpose of use, and the taste of a medical person who is the user of the monitor.

When the setting of a bedside monitor is to be changed, an operation menu for performing a desired operation must be displayed on a screen, and the menu must be selected. However, a usual bedside monitor is equipped with various functions, and therefore it is impossible to display all operation menus at a time on one screen. In a bedside monitor, therefore, a menu is hierarchized, and it sometimes occurs that an objective operation cannot be selected unless a deep hierarchy is selected.

Some types of bedside monitors are provided with a menu customizing function in which three menus that are frequently used can be registered at a maximum as shortcut menus, and displayed in an upper portion of a typical image (basic screen). According to this function, the selection of the objective operation menu can be performed not in a hierarchical menu but on the basic screen, and therefore the operability is improved.

Usually, there is a possibility that a transportable bedside monitor is used while being moved among various diagnosis departments. In the case where the same bedside monitor is used in sites such as a surgery room and an ICU, in diagnosis departments such as a cardiovascular department and a neurology department, or in job categories such as a nurse and a medical technologist, for example, operations to be registered as shortcut menus may be largely different. However, it is considered that an operation in which a shortcut menu is freely registered at an individual user level is problematic. Therefore, it is usual that setting of a shortcut menu is allowed to only an apparatus administrator who knows a password.

However, a system in which, each time a bedside monitor is moved to another place, the administrator is requested to change a shortcut menu cannot be practically employed. Therefore, it is requested to develop a bedside monitor provided with a shortcut menu which is easier to use.

SUMMARY

The presently disclosed subject matter may provide a biological information displaying apparatus which, even when a change of a shortcut menu is restricted, can provide a shortcut menu that is easy for the user to use.

The biological information displaying apparatus which is configured to display biological information measured by a sensor adapted to be attached to a patient, may comprise: a displaying unit which is configured to display the biological information on a screen; an operation menu storing unit which is configured to store a plurality of operation menus for operating the biological information displaying apparatus; an operation menu priority determining unit which is configured to determine priorities of the operation menus stored in the operation menu storing unit, based on a predetermined condition; and a preferential-shortcut menu displaying unit which, based on the priorities determined by the operation menu priority determining unit, is configured to select a first part of the operation menus as a first shortcut menu, and which is configured to display the first shortcut menu on the screen.

DETAILED DESCRIPTION OF EXEMPLARY EMBODIMENTS

External Appearance of Bedside Monitor

Figure 1:
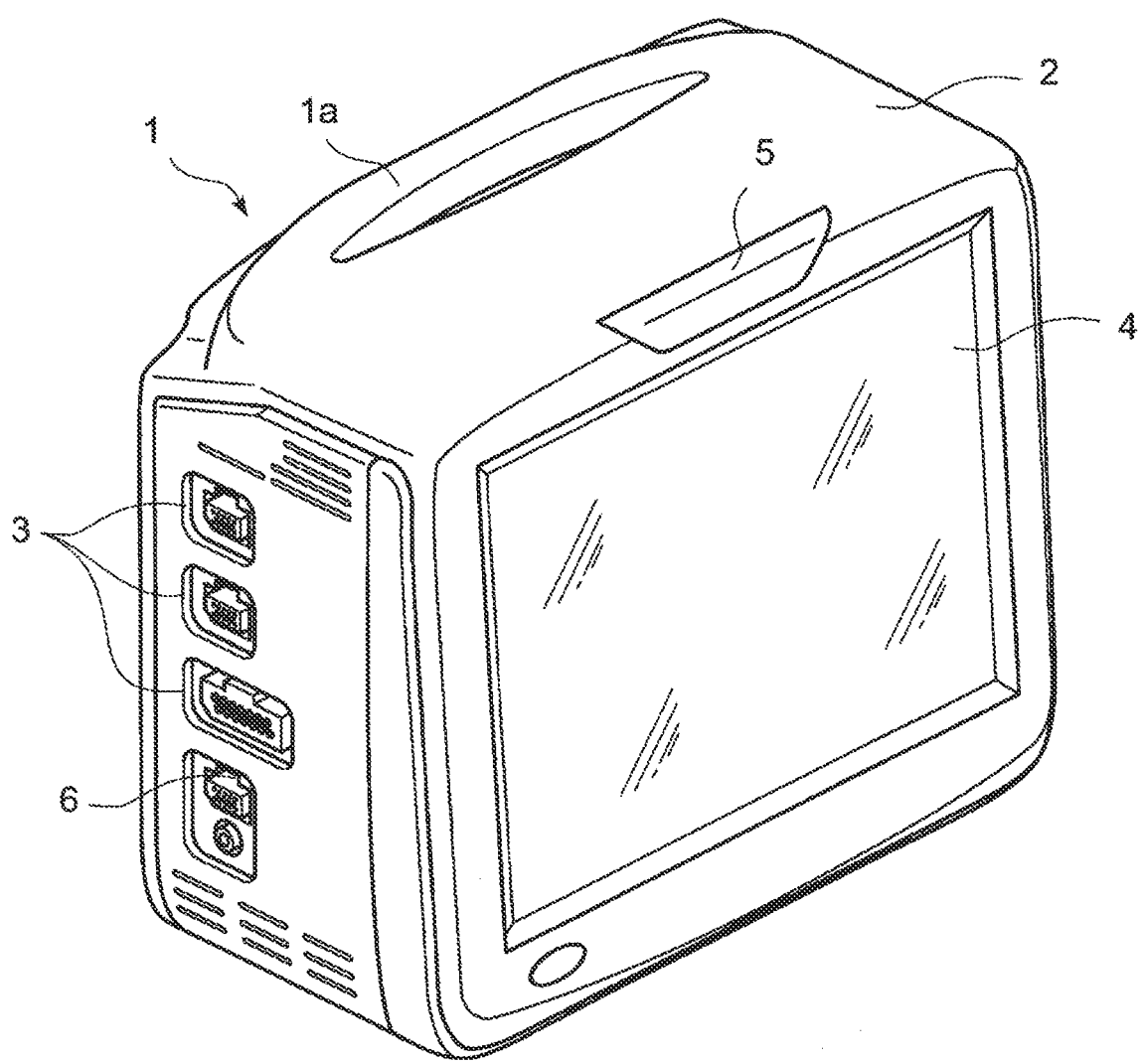
FIG. 1 is an external view of a bedside monitor of an embodiment of the presently disclosed subject matter.

FIG. 1 is an external view showing a bedside monitor 1 of an embodiment of the biological information displaying apparatus of the presently disclosed subject matter.

The bedside monitor 1 has a relatively small housing 2 in which a carrying handle 1a is disposed on the upper back surface side. The whole configuration including hardware and software for monitoring biological information of the patient is mounted in the housing 2. A multi-port interface 3 to which various sensors attached to the patient are to be connected, and an output interface 6 are disposed in a side surface of the housing 2, and a touch panel display 4 which displays biological information (vital sign) of the patient in a manner easily visible to the user is disposed on the front surface. In the housing 2, a light emitting section 5 for warning is disposed above the display 4, and a speaker which is not shown is disposed in the housing.

Figure 2:
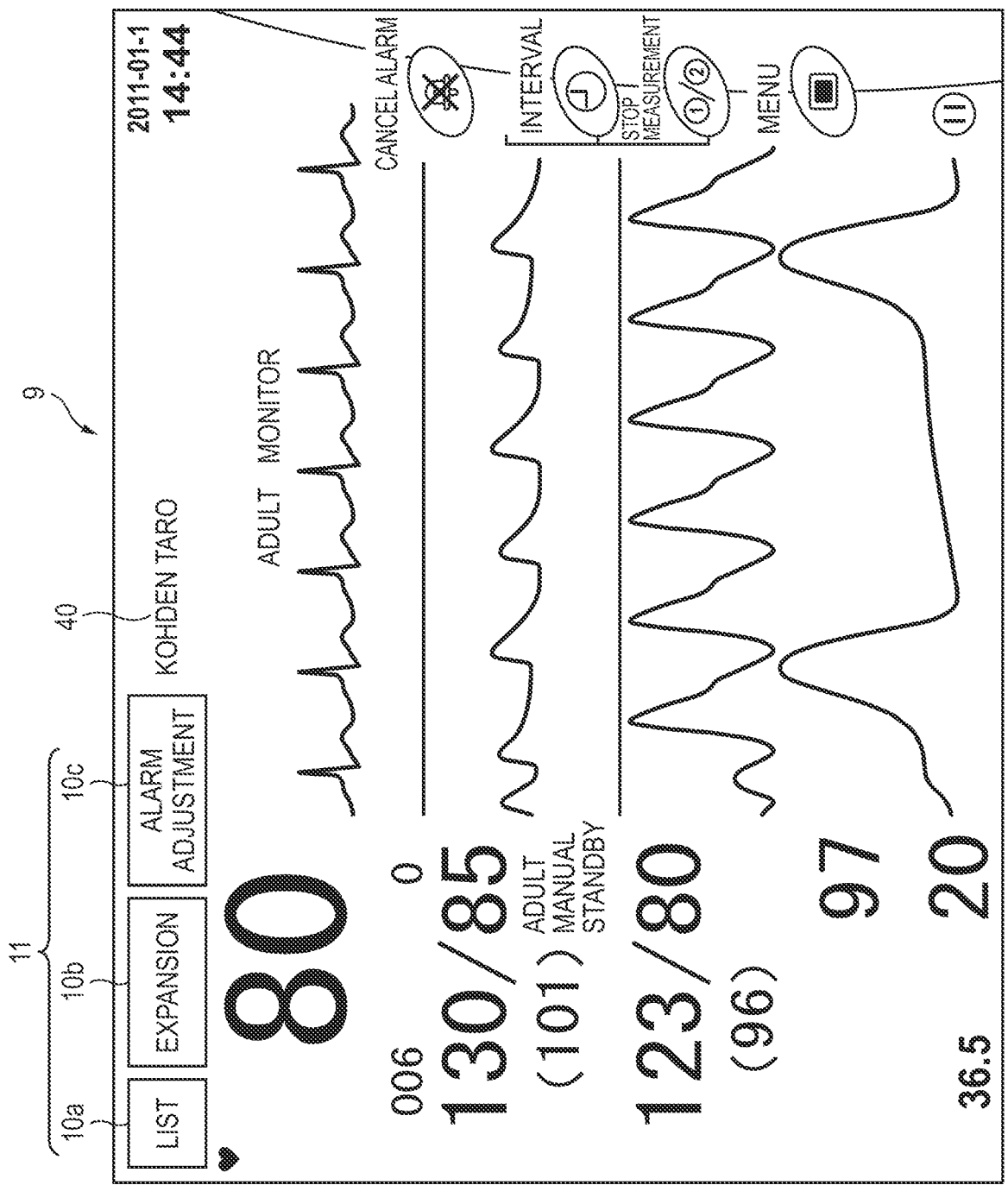
FIG. 2 is a view showing a display example of a typical screen in the embodiment.

FIG. 2 shows a display example of a biological information screen 9 which is displayed on the display 4. On the biological information screen 9, for example, parameters, i.e., an electrocardiogram, impedance respiration, a non-invasive blood pressure, an arterial oxygen saturation, the body temperature, an invasive blood pressure, and the carbon dioxide partial pressure are shaped and displayed in formats which are easily visibly recognized by a medical person functioning as the user. A shortcut menu displaying portion 11 is disposed in the upper left corner of the biological information screen 9, and three operation menus 10a to 10c which are selected in order to easily access respective functions of the bedside monitor 1 are always displayed as shortcuts.

The presently disclosed subject matter relates to improvements of selection, display, and updation of the operation menus 10a to 10c which are displayed in the shortcut menu displaying portion 11. Hereinafter, a configuration for realizing them will be described in detail with reference to FIG. 3 and subsequent figures.

(System Configuration of Bedside Monitor)

Figure 3:
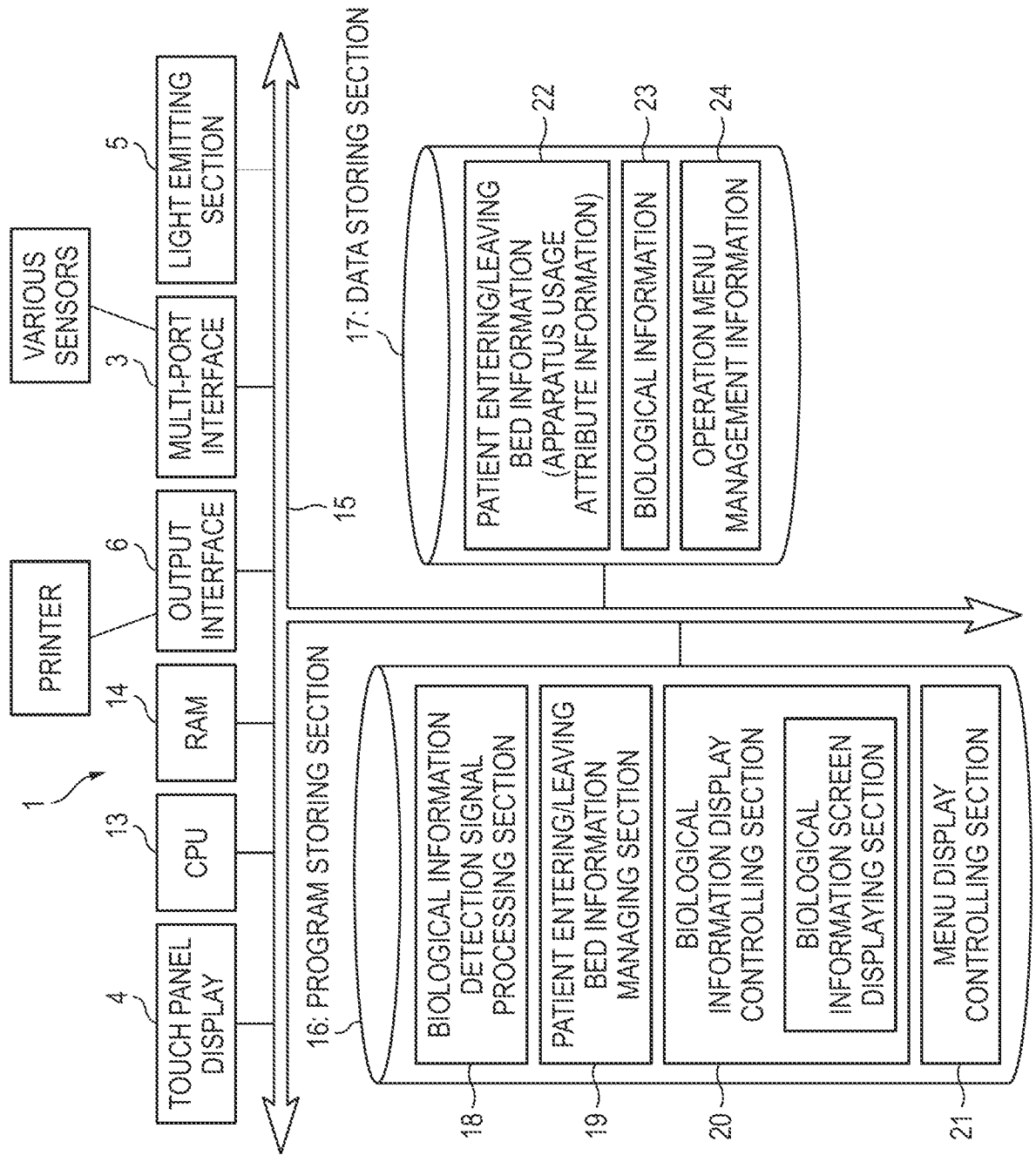
FIG. 3 is a diagram showing the system configuration of the bedside monitor.

FIG. 3 is a diagram showing the system configuration of the bedside monitor 1 of the embodiment.

The bedside monitor 1 is configured by connecting a program storing section 16 and data storing section 17 which are configured by a recording medium such as a hard disk, to a main bus 15 to which the display 4, a CPU 13, a RAM 14, the output interface 6, the multi-port interface 3, and the warning devices (the light emitting section 5 and the speaker) are connected.

The program storing section 16 stores a basic program (an OS and the like, not shown), and further stores: a biological information detection signal processing section 18 which outputs parameters indicating biological information based on detection signals output from the various sensors attached to the patient; a patient entering/leaving bed information managing section 19 for inputting the usage attribute of the apparatus; a biological information display controlling section 20 which processes the parameters indicating the biological information to produce various display screens including the biological information screen 9; and a menu display controlling section 21 which controls the shortcut menu displaying portion 11. The data storing section 17 stores patient entering/leaving bed information 22 which is apparatus usage attribute information, biological information 23 including the above-described parameters, and operation menu management information 24 which is necessary for displaying shortcut menus and operation menus.

Figure 4:
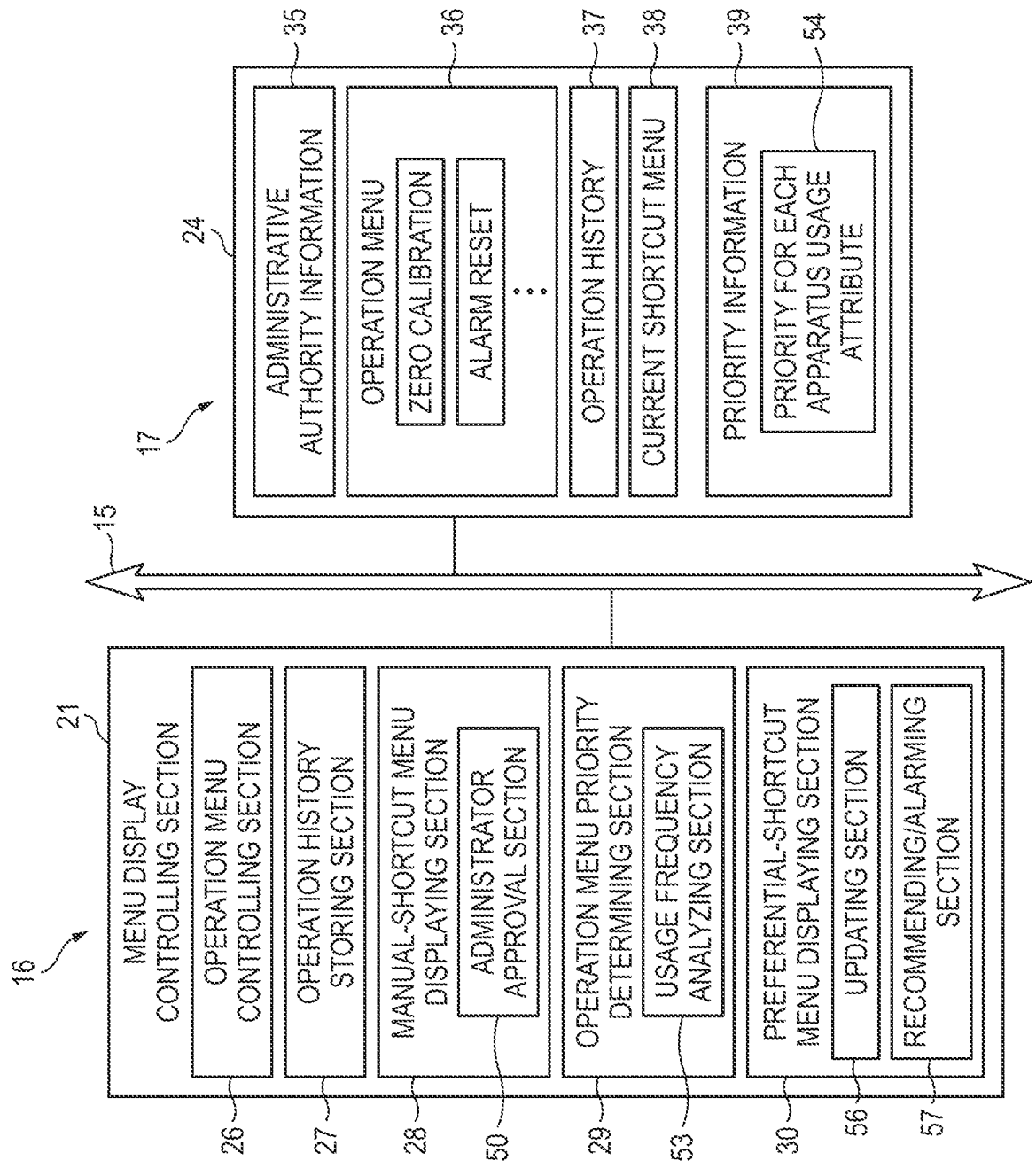
FIG. 4 is a diagram showing the system configuration of the bedside monitor.

FIG. 4 is a diagram showing in further detail the menu display controlling section 21 and the operation menu management information 24.

The menu display controlling section 21 has an operation menu controlling section 26, an operation history storing section 27, a manual-shortcut menu displaying section 28, an operation menu priority determining section 29, and a preferential-shortcut menu displaying section 30. The operation menu management information 24 stored in the data storing section 17 has administrative authority information 35, operation menus 36, operation history information 37, a current shortcut menu 38, and operation menu priorities 39.

In practice, the components 18 to 21 (FIG. 3) and 26 to (FIG. 4) stored in the program storing section 16 are realized by computer software programs, called on the RAM 14 by the CPU 13, and then expanded and executed, so that the programs appropriately access the data 22 to 24 (FIG. 3) and 35 to 39 (FIG. 4) stored in the data storing section 17 and function as the components set forth in the claims.

Hereinafter, the configurations of the components 18 to 21 and 26 to 30 will be described in detail by describing their operations.

(Biological Information Detection Signal Processing Section)

Firstly, the biological information detection signal processing section 18 (FIG. 3) has a function of processing signals output from the sensors connected to the multi-port interface 3, and outputting the biological information 23.

For example, an electrocardiogram cable (functioning also as a respiratory sensor), an invasive blood pressure cable, a body temperature probe, an SpO2 (pulse oximeter) probe, a cuff for measuring a non-invasive blood pressure, a capnography sensor, and the like are connected to the multi-port interface 3. Therefore, the biological information detection signal processing section 18 outputs parameters, i.e., an electrocardiogram, impedance respiration, a non-invasive blood pressure, an arterial oxygen saturation, the body temperature, an invasive blood pressure, and the carbon dioxide partial pressure. The parameters are stored as the biological information 23 in the data storing section 17 (FIG. 3).

(Patient Entering/Leaving Bed Information Managing Section)

The patient entering/leaving bed information managing section 19 (FIG. 3) performs a function of acquiring the usage attributes of the apparatus.

Figure 5:
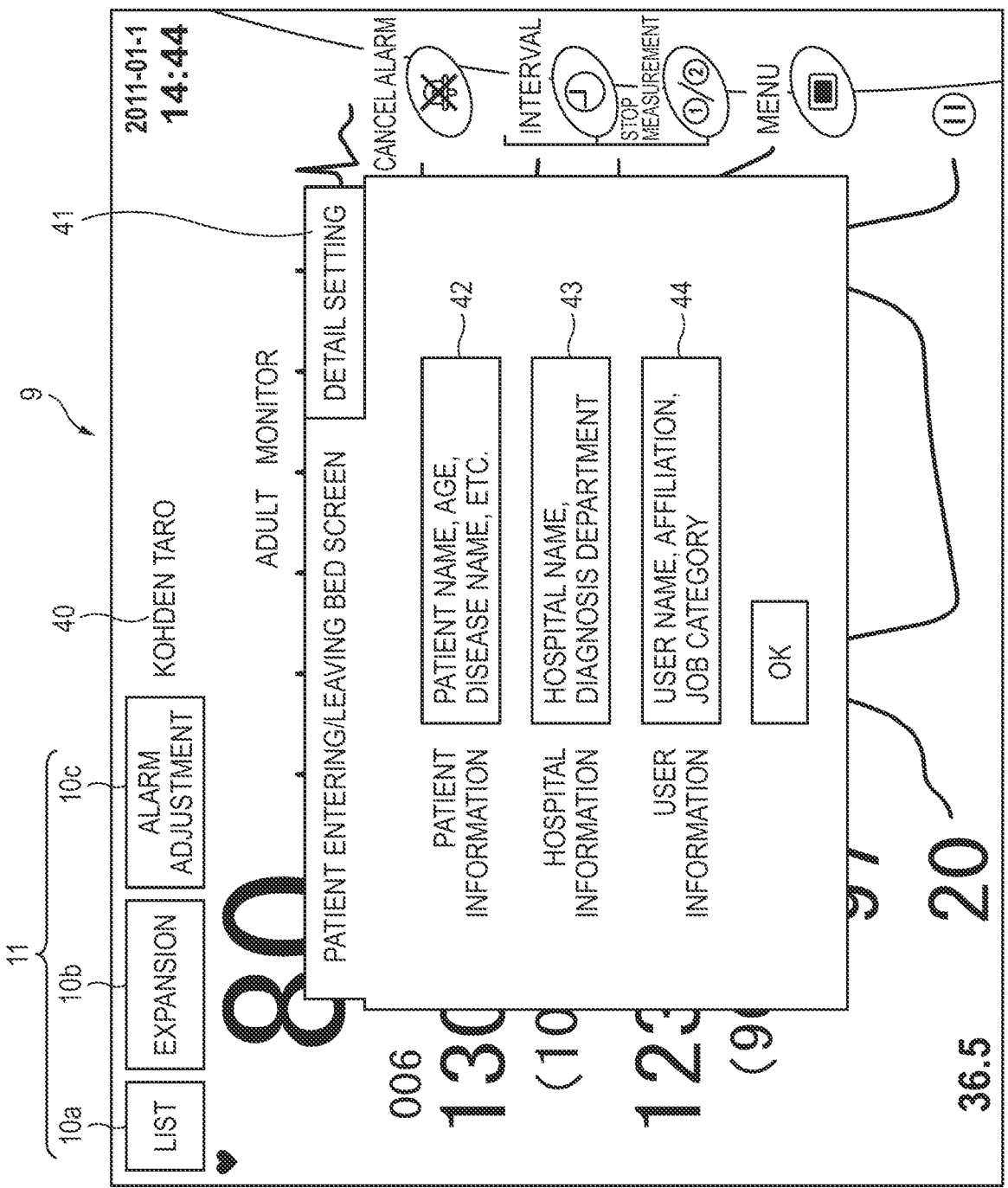
FIG. 5 is a view showing a display example of a patient entering/leaving bed screen.

When a portion 40 (portion where "KOHDEN Taro" is displayed in FIG. 2) of the patient name displayed in the upper portion of the biological information screen 9 is touched with the fingertip, the patient entering/leaving bed information managing section 19 displays a patient entering/leaving bed screen 41 such as shown in FIG. 5, in a pop-up manner. Patient information (the name, the classification, the age, the sex, etc.) 42, hospital information (medical ward information, etc.) 43, and user information (the user ID, the job category, etc.) 44 are input on the pop-up displayed patient entering/leaving bed screen 41. In the embodiment, as the medical ward information, one of four wards, i.e., "Adult ward", "Child ward," "Neonatal ward," and "Adult/child ward" can be selected by default. As the job category of the user, one of two jobs, i.e., "Nurse" and "Doctor" can be selected by default. The patient information 42, the hospital information 43, and the user information 44 may be manually input, or, in the case where the information is previously registered in a database, searched in the database and then set.

The patient entering/leaving bed information managing section 19 stores the patient entering/leaving bed information 22 which is set on the pop-up displayed patient entering/leaving bed screen 41, in the data storing section 17 as the apparatus usage attribute information (see FIG. 3).

(Biological Information Display Controlling Section)

Next, the biological information display controlling section 20 (FIG. 3) processes the parameters (biological information 23) output from the biological information detection signal processing section 18, produces the biological information screen 9 shown in FIG. 2, and graphically displays the biological information screen 9 on the touch panel display 4. Specifically, when a cable extending from a sensor attached to the patient is connected to the multi-port interface 3, the measurement is automatically started, and the section displays a result of the measurement on the biological information screen 9 in the form of a waveform, numerals, or a symbol. When "New measurement item of biological information" is added, an additional information display is automatically laid out in the biological information screen 9. In the embodiment, the touch panel display 4 is employed, and therefore the user can select one of various functions with one touch of the fingertip.

(Menu Display Controlling Section)

Next, operations of the operation menu controlling section 26, operation history storing section 27, manual-shortcut menu displaying section 28, operation menu priority determining section 29, and preferential-shortcut menu displaying section 30 which constitute the menu display controlling section 21 will be described in detail with reference to FIG. 4 and subsequent figures.

(Operation Menu Controlling Section)

Figure 6:
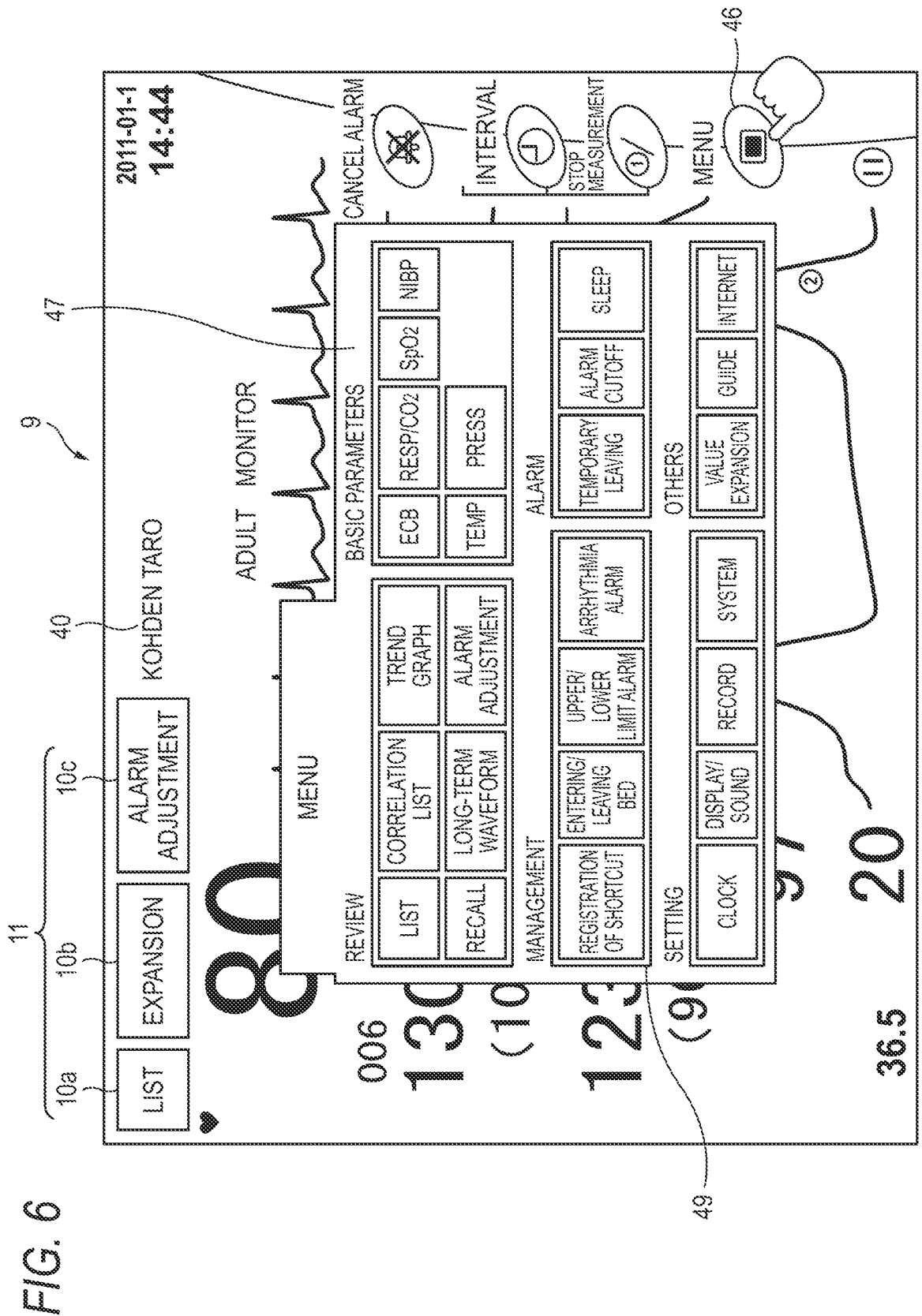
FIG. 6 is a view showing a display example of an operation menu selection screen.

Firstly, the operation menu controlling section 26 (FIG. 4) has a function of displaying various operation menus for operating the bedside monitor 1. Specifically, when a menu button 46 on the biological information screen 9 is touched as shown in FIG. 6, the operation menus 36 stored in the data storing section 17 is taken out, and a pop-up screen 47 is displayed on the biological information screen 9 as shown in FIG. 6. In the embodiment, all of the operation menus 36 cannot be displayed on the single pop-up screen 47, and therefore several ones of the operation menus are hierarchically selected. In this case, when one operation menu is selected in the screen of FIG. 6, another similar pup-up screen (similar to the screen 47) is opened, and further options are displayed. The user selects a desired operation menu from the pup-up screen 47, and then can perform various settings.

(Operation History Storing Section)

The operation history storing section 27 (FIG. 4) has a function of storing the selection of the operation menu which is performed in the above, as the operation history 37 in the data storing section 17. The operation history 37 is stored in association with the patient entering/leaving bed information 22 (apparatus usage attribute) which is input in the patient entering/leaving bed information managing section 19. Namely, the operation history is stored in association with the information of the patient information 42, the hospital information (medical ward) 43, and the user information 44.

(Manual-Shortcut Menu Displaying Section)

Figure 7:
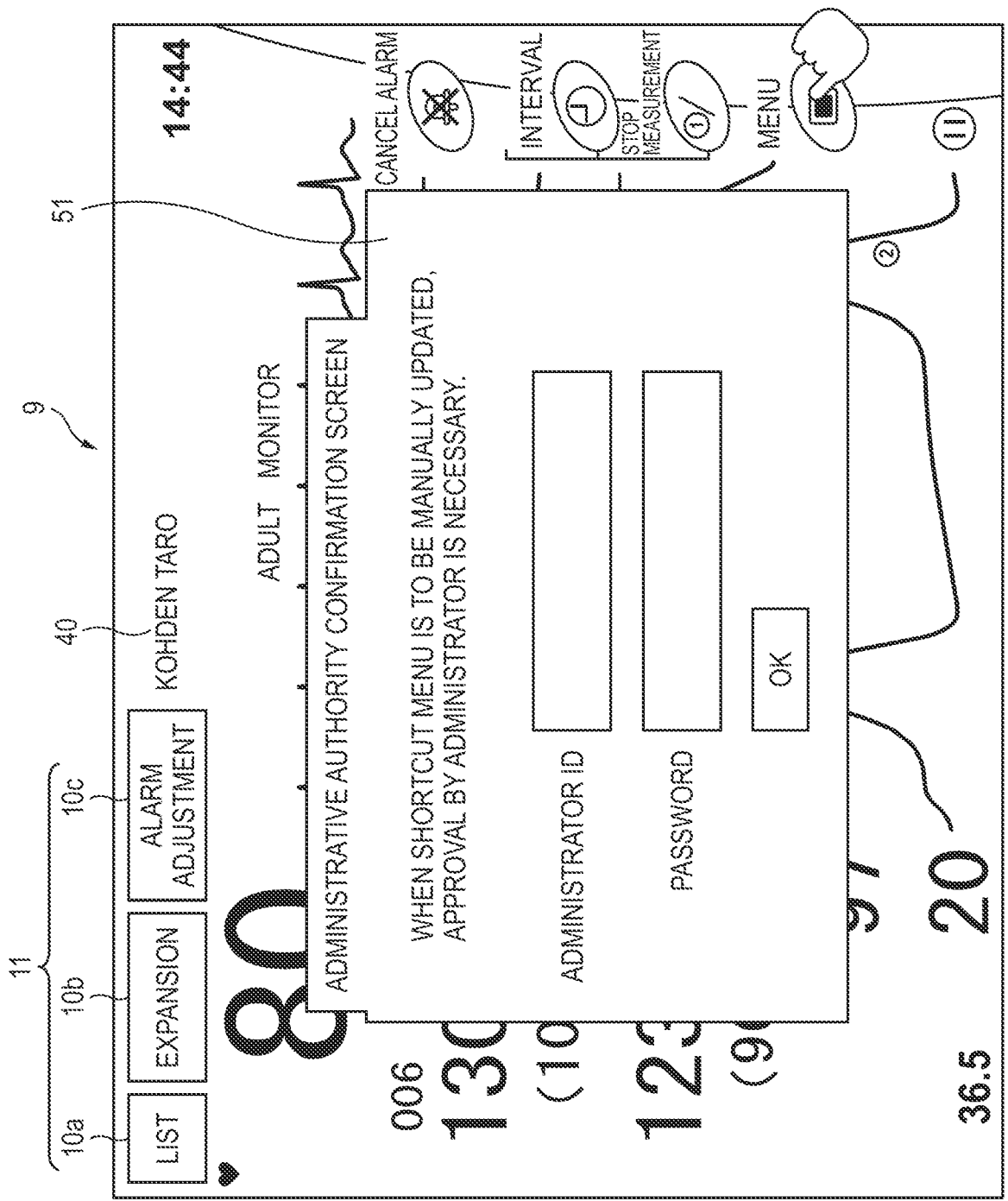
FIG. 7 is a view showing a display example of an administrative authority confirmation screen.

The manual-shortcut menu displaying section 28 (FIG. 4) has a function of, under the authority of the apparatus administrator, causing a part of the operation menus 36 to be manually selected as shortcut menus, and displaying the shortcut menu on the shortcut menu displaying portion 11 of the biological information screen 9. Specifically, when the menu of "Registration of shortcut menu" 49 is selected from the pup-up screen 47 shown in FIG. 6 for selecting the operation menu, a selection screen which is not shown is opened, and an operation menu which is to be registered as a shortcut can be selected from the selection screen. In the embodiment, the manual-shortcut menu displaying section 28 has an administrator approval section 50, and, after approval by the administrative authority is obtained based on the administrative authority information 35, manual registration of the shortcut menu can be completed. Specifically, before or after a shortcut is manually set, an administrative authority confirmation screen 51 such as shown in FIG. 7 is displayed in a pop-up manner, and the manual setting of the shortcut is enabled after approval through the administrative authority confirmation screen 51.

The shortcut menu which is manually selected in the above is stored as the current shortcut menu 38 in the data storing section 17, and the selected operation menu is always displayed in the shortcut menu displaying portion 11 which is disposed in the upper left portion of the biological information screen 9.

According to the shortcut menu displaying portion 11 which has been set as described above, even when the pup-up screen 47 of operation menus such as shown FIG. 6 is not hierarchically displayed every time, the basic screen can be transferred to one of various setting screens without effort by a single operation. When the shortcut menu is frequently changed, however, the user may be disturbed. In the embodiment, therefore, the administrative authority confirmation screen 51 (FIG. 7) which is password managed is disposed, and only the apparatus administrator can change shortcut menus.

(Operation Menu Priority Determining Section)

The operation menu priority determining section 29 (FIG. 4) has a function of determining the priorities of the operation menus 36 held in the data storing section 17, based on predetermined conditions.

In the embodiment, the operation menu priority determining section 29 takes out the menu operation history 37 from the data storing section 17, and determines the priorities of the operation menus based on one or a plurality of the latest degree, degree of importance, and number of uses of respective operation menus. Specifically, the operation menu priority determining section 29 has a usage frequency analyzing section 53, and determines the priorities of the operation menus by using preset menu recommendation algorithm.

(Usage Frequency Analyzing Section)

The usage frequency analyzing section 53 performs a process of analyzing individual operation menus in terms of three points or the latest degree, the degree of importance, and the number of uses, and giving a score to them.

Specifically, predetermined weighting is performed on the indexes or the latest degree, the degree of importance, and the number of uses, and the values after the weighting are added together to calculate a total score. Then, a ranking of the scores is produced, and superior operation menus are output as menus which are recently heavily used many times, i.e., menus which are important and frequently used. The importance and meaning of each index are varied depending on the usage attribute such as the patient and the medical ward. In the embodiment, therefore, the weighting on the indexes are predetermined in association with the apparatus usage attribute 22. In place of the use of the three indexes, a combination of two indexes or only one index may be used.

More Specifically, the usage frequency analyzing section 53 classifies each of the indexes (into, for example, five ranks), produces a matrix in which the three indexes are combined (in the case of five ranks, for example, a matrix which is divided into 5×5×5=125 "cells"), and segments each operation menu in accordance with the belonging cell in the matrix.

A menu having high scores with respect to all indexes is determined as an operation menu which is high in use value for the user, the medical ward, or the diagnosis department. When, for each of the three items, weighting is set in accordance with the characteristics of the user, the medical ward, the diagnosis department (apparatus usage attribute 22), menus which are important and frequently used in the use environment can be determined.

The weighting coefficient for each apparatus usage attribute 22, and the score and ranking 54 of each operation menu for each usage attribute which are determined in the above-described process are output as the priority information 39, and stored in the data storing section 17.

(Preferential-Shortcut Menu Displaying Section)

The preferential-shortcut menu displaying section 30 (FIG. 4) has a function of, based on the priority information 39 determined by the operation menu priority determining section 29, selecting a part of the plurality of operation menus 36 as shortcut menus, and displaying the menu in the shortcut menu displaying portion 11 on the biological information screen 9. The preferential-shortcut menu displaying section 30 selects a part of the plurality of operation menus 36 as shortcut menus, regardless of administrator approval and based only on the priorities 39, and displays the menus on the biological information screen 9.

(Updating Section)

The preferential-shortcut menu displaying section 30 has an updating section 56 (FIG. 4). The updating section 56 has a function of causing the operation menu priority determining section 29 to reexecute the frequency analysis at a predetermined timing, and updating the priorities 39 of the operation menus. Based on the updated priorities 39, the preferential-shortcut menu displaying section 30 updates the display of the shortcut menu displaying portion 11 on the biological information screen 9.

In the default setting, the timing of executing the updation process is the timing when the bedside monitor 1 is booted, and that when the patient entering/leaving bed information (apparatus usage attribute) 22 is updated. The administrator can arbitrarily change or set the execution timing.

(Recommending/Warning Section)

Figure 8:
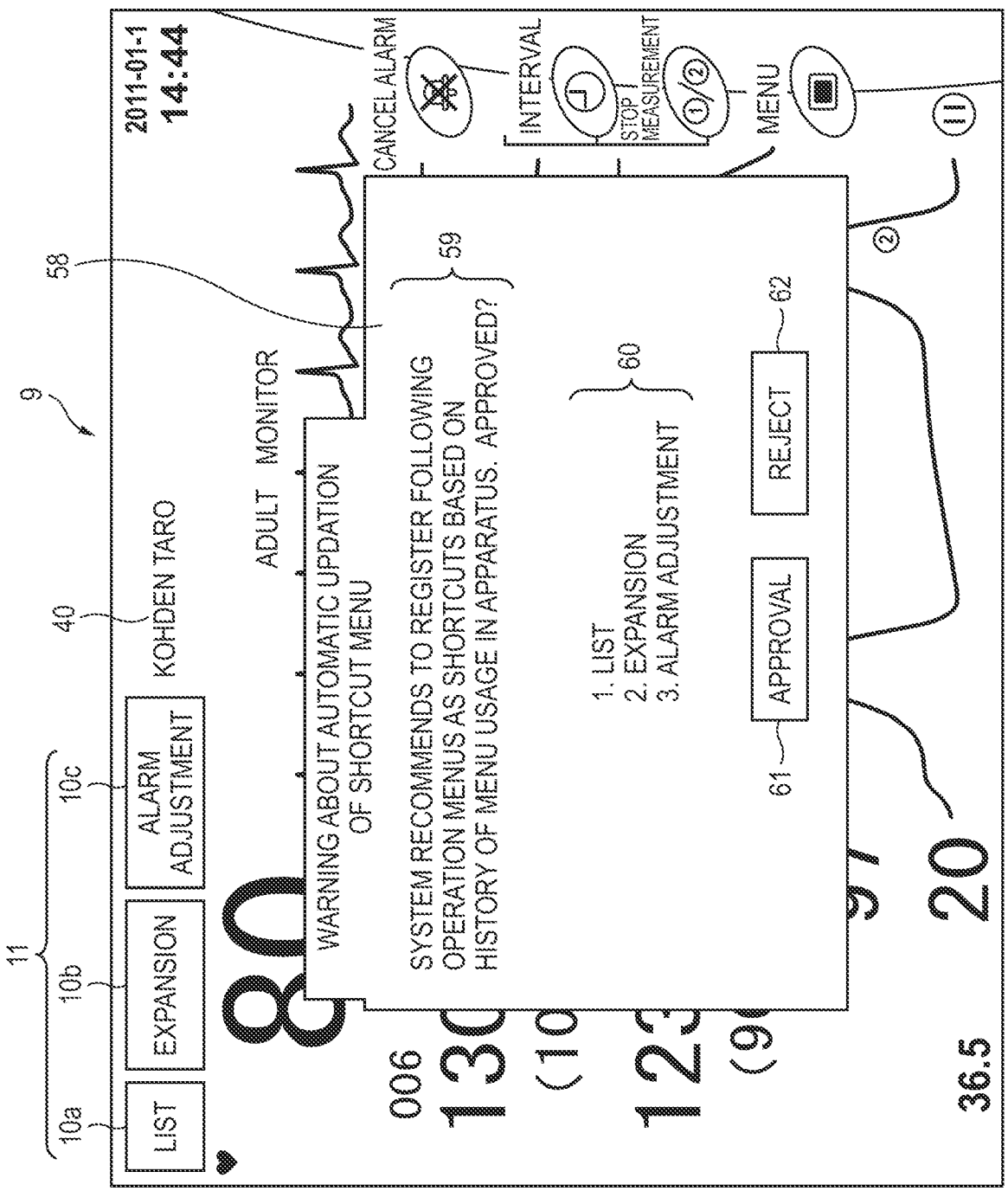
FIG. 8 is a view showing a display example of a recommending/warning screen.

The embodiment has a recommending/alarming section 57 which, when the shortcut menus are to be updated by the updating section 56, recommends the new preferential-shortcut menus and gives warning of updation. The recommending/alarming section 57 displays a recommending/warning screen 58 such as shown in FIG. 8 on the biological information screen 9 in a pop-up manner, to prompt the user to approve the updation. The recommending/warning screen 58 includes a predetermined warning statement 59, and also a list 60 of three operation menus having higher priority, an approval button 61, and a rejection button 62. Only when the user presses the approval button 61, the updation by the updating section 56 is executed.

According to the above-described functions, a menu having a high frequency of usages by the user can be determined by the frequency analysis, and shortcut menus can be dynamically changed based on the determination. Therefore, shortcut menus which are suitable for the place of use and the purpose of use can be registered without bothering the apparatus administrator.

Before the change is actually performed, a message requesting the user to allow the change is displayed. Therefore, the shortcut menus can be prevented from being changed despite the intention of the current user.

According to an aspect of the presently disclosed subject matter, the message to the user is not appropriately displayed, but displayed at proper timings such as those when the apparatus has been booted but not yet used, or when a patient newly enters the bed. Therefore, a trouble such as that in which a work is interrupted by a pop-up display performed during the course of the work can be prevented from occurring.

According to an aspect of the presently disclosed subject matter, the usage frequency is analyzed for each of the apparatus usage attributes including the patient information, the hospital information, and the user information, whereby candidates for shortcut menus are determined for each of users and places of use, and shortcut menus are changed in accordance with the user and the place of use. According to the configuration, in conjunction with the diagnosis department, the job category, and the like, three high-order operation menus which are frequently used by nurses, or those which are frequently used in an ICU are recommended, and therefore it is possible to realize a user interface which is dedicated to the operator, and which is easier to use.

According to the configuration, even in the case where a shortcut is not initially set by the user, a frequently used button is automatically recommended as a result of repeated uses. Even when the operation does not enter a deep hierarchy which is managed by using a password, therefore, a shortcut can be automatically set. In the case where such recommendation is not necessary, the recommendation may be rejected.

According to an aspect of the presently disclosed subject matter, even in the case where the apparatus is used in various usage modes, a shortcut menu can be registered with switching the priority of the operation menu for each of the plurality of apparatus usage attributes.

In this case, it is more preferable that, when the shortcut menu is to be updated, a message requesting the user to approve a change is displayed, and, only when approval is received from the user, the updation is performed. Therefore, a situation such as that, during the work, updation of a shortcut menu, or an unexpected change of display of a shortcut menu is performed can be prevented from occurring.

The invention is not limited to the above-described embodiment, and may be variously modified within a scope not changing the gist of the invention.

For example, the biological information displaying apparatus is not limited to the bedside monitor 1 having the configuration such as shown in FIG. 1, and may have another configuration. For example, the apparatus may have a configuration where a monitor and a controller are separately formed, or where a touch panel display is not disposed, and a usual display and inputting means such as a mouse or a keyboard are used.

In the case where a pop-up menu itself is not necessary, the apparatus may be configured so that the automatic pop-up menu can be cancelled. The method of acquiring the apparatus usage attribute information may be performed so that the information is recognized and acquired by magnetic means or wireless or another type of communication means while using an ID card or an electronic tag.

In the embodiment, the conditions for determining the priority by the operation menu priority determining section 29 are those based on one or a plurality of the latest degree, degree of importance, and number of uses of each operation menu. The conditions may be based on another index(es). The determination of the priority of the operation menu is executed by preset menu recommendation algorithm. The determination method is not limited to this. In the determination, alternatively, another method may be employed, or the bedside monitor 1 itself may not perform the analysis, and may receive on-line the priority information 39 from an external server or the like.

What is claimed is:

1. A biological information displaying apparatus which is configured to display biological information measured by a sensor adapted to be attached to a patient, the biological information displaying apparatus comprising at least one processor and memory configured to:
- display the biological information on a screen;
- store a plurality of operation menus for operating the biological information displaying apparatus;
- acquire information related to apparatus usage attribute including patient information or hospital information;
- determine priorities of the operation menus based on a score calculated by performing weighting on at least one of a latest degree, a degree of importance, or a usage frequency, which are indicated in a selection history of the operation menus, the weighting being in accordance with the information related to the apparatus usage attribute; and
- select a first part of the operation menus as a first shortcut menu, and display the first shortcut menu on the screen based on the determined priorities, wherein:
- the at least one processor and memory are configured, under approval of an administrator of the biological information displaying apparatus, to cause a second part of the operation menus to be manually selected as a second shortcut menu and to display the second shortcut menu on the screen,
- when the second part of the operation menus is manually selected as the second shortcut menu, a screen to obtain the approval of the administrator is displayed, and
- the at least one processor and memory are configured to select the first part of the operation menus as the first shortcut menu, regardless of the approval of the administrator and based only on the priorities, and to display the first shortcut menu on the screen.

2. The biological information displaying apparatus according to claim 1, wherein the at least one processor and memory are configured to: store the selection history of the operation menus, and receive the stored selection history, and determine the priorities of the operation menus.

3. The biological information displaying apparatus according to claim 1, wherein the at least one processor and memory are configured to:
- update the priorities of the operation menus at a predetermined timing, and
- select, based on the updated priorities, a third part of the operation menus as a third shortcut menu, and update a shortcut menu displayed on the screen to the third shortcut menu.

4. The biological information displaying apparatus according to claim 3, wherein a timing when the shortcut menu displayed on the screen is updated when the biological information displaying apparatus is booted.

5. The biological information displaying apparatus according to claim 1, wherein, when the information related to the apparatus usage attribute acquired is changed, the at least one processor and memory are configured to update the shortcut menu displayed on the screen, based on the priorities which are determined based on the changed information related to the apparatus usage attribute.

6. The biological information displaying apparatus according to claim 5, wherein,
- when updating the shortcut menu displayed on the screen, the at least one processor and memory are configured to display a message requesting a user to approve a change, and,
- only when receiving approval from the user, the at least one processor and memory are configured to update the shortcut menu displayed on the screen.

7. A biological information displaying apparatus which is configured to display biological information measured by a sensor adapted to be attached to a patient, the biological information displaying apparatus comprising at least one processor and memory configured to:
- display the biological information on a screen;
- store a plurality of operation menus for operating the biological information displaying apparatus;
- acquire information related to apparatus usage attribute including patient information or hospital information;
- determine priorities of the operation menus based on a score calculated by performing weighting on at least one of a latest degree, a degree of importance, or a usage frequency, which are indicated in a selection history of the operation menus, the weighting being in accordance the information related to the apparatus usage attribute;
- update the priorities of the operation menus; and
- select a first part of the operation menus as a first shortcut menu, and which is configured to display the first shortcut menu on the screen based on the determined priorities, wherein:
- the at least one processor and memory are configured, under approval of an administrator of the biological information displaying apparatus, to cause a second part of the operation menus to be manually selected as a second shortcut menu and to display the second shortcut menu on the screen,
- when the second part of the operation menus is manually selected as the second shortcut menu, a screen to obtain the approval of the administrator is displayed, and
- the at least one processor and memory are configured to select the first part of the operation menus as the first shortcut menu, regardless of the approval of the administrator and based only on the priorities, and to display the first shortcut menu on the screen.

8. The biological information displaying apparatus according to claim 7, wherein the at least one processor and memory are configured to store the selection of the operation menus displayed.

9. The biological information displaying apparatus according to claim 1,
- wherein the screen includes a shortcut menu displaying portion;
- the at least one processor and memory configured to select based on the determined priorities are configured to select which menus are to be displayed on the screen; and
- the at least one processor and memory configured to display the biological information are configured to display the selected menus in the shortcut menu displaying portion.

10. The biological information displaying apparatus according to claim 7,
- wherein the screen includes a shortcut menu displaying portion;
- the at least one processor and memory configured to select based on the determined priorities are configured to select which menus are to be displayed on the screen; and
- the at least one processor and memory configured to display the biological information are configured to display the selected menus in the shortcut menu displaying portion.

11. The biological information displaying apparatus according to claim 1, wherein the patient information includes a name, a classification, an age, or a sex.

* * * * *